United States Patent [19]

Drewlow

[11] Patent Number: Plant 6,418

[45] Date of Patent: Nov. 22, 1988

[54] STREPTOCARPUS PLANT NAMED JANUS

[75] Inventor: Lyndon W. Drewlow, Ashtabula, Ohio

[73] Assignee: Mikkelsens, Inc., Ashtabula, Ohio

[21] Appl. No.: 9,378

[22] Filed: Jan. 30, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Streptocarpus plant named Janus characterized by its compact growth habit, rosette form, violet blue flower color, floriferous habit, small pliable leaves, ease of propagation, and by its long lasting and non-shattering flowers.

1 Drawing Sheet

The present invention relates to a new and distinct cultivar of Streptocarpus plant, botanically known as *Streptocarpus*×*hybridus*, and known by the cultivar name Janus. Janus was developed by me through controlled breeding by crossing Mikkelsen Seedling 82-1015-30 (seed parent)×Mikkelsen Seedling 82-1069-30 (pollen parent).

Asexual reproduction by me by leaf cuttings has shown that the unique features of this new streptocarpus are stabilized and are reproduced true to type in successive propagations.

The following characteristics distinguish the new Streptocarpus from both its parent varieties and other cultivated streptocarpus of this type known and used in the floriculture industry:

1. Janus is a mid-blue flower, being similar in color to Pluto; deeper blue than Orion, and lighter blue than both Minerva and Neptune. Orion and Minerva are disclosed in pending plant applications, as are the cultivars Muse, Pegasus, Electra, Ulysses and Achilles referred to below. Pluto and Neptune are know but unpatented cultivars, as are the cultivars Snowdrop and Diana noted below.

2. Janus has smaller flowers than Pluto but many more flowers open at one time. Thus the net effect is more color in Janus. The flowers are also smaller than Minerva and similar to Neptune, but do not cup like Neptune.

3. From a well rooted plant out of a 72 cell pack a well developed flowering plant can be obtained in 6 to 8 weeks in a 10 cm pot, making it 7 to 10 days earlier than Pluto.

4. Janus produces numerous plantlets from leaf cuttings in 8 to 10 weeks. It, along with Orion and Diana are the best propagators.

5. Leaf size is smaller than Pluto making it easier to ship. Leaves are not as coarse as Neptune. Leaves are similar to Orion and Muse.

6. Plants of Janus are not as compact as Minerva, Neptune and Pegasus, are similar in that characteristic to Orion, Electra and Muse, and is more compact than Ulyssus and Achilles.

7. Janus has shown the ability to flower both under the low light conditions of winter (December to February) and under the higher temperatures of summer (July to September), which many of the older cultivars such as Snowdrop do not.

8. Janus also has the ability to tolerate watering with colder than normal water (40° F.) without foliar spotting, and to tolerate fairly high light levels in summer without leaf yellowing or bronzing, which is not the case for Snowdrop.

9. Janus is characterized by its numerous short leaves in a rosette instead of one large leaf that characterize many streptocarpus cultivars. This results in a cluster of flowers in the middle of green foliage making an attractive 10 cm flowering plant.

10. Janus at one time may have 4 to 5 flower stalks in various stages of development, while Pluto may have only 1 or 2.

The accompanying color photograph illustrates in perspective view the overall appearance of Janus, with colors being as true as it is reasonably possible to obtain in a color reproduction of this type.

The following is a detailed description of my new Streptocarpus cultivar based on plants produced under commercial practices in Greenhouses of Mikkelsens Inc., Ashtabula, Ohio. Color references are made to The Royal Horticultural Society Color Chart (R.H.S.), except where general colors of ordinary dictionary significance are used.

Classification:

*Botanical.*—*Streptocarpus*×*hybridus*, cv. Janus.

Parentage: Controlled cross between Mikkelsen seedling 82-1015-30 and Mikkelsen seedling 82-1069-30.

Propagation:

A. *Type cutting.*—Leaf.

B. *Time to develop plantlets.*—*Summer:* 8 weeks at 20° C.; Winter: 10 weeks at 20° C.

C. *Rooting habit:* Numerous, fine, fibrous.

Plant description:

A. *Form.*—Leaves rosette in form, extending from a crown at the soil line with flower stalks forming at the leaf midrib. Many leaves in a symmetrical pattern.

B. *Habit of growth.*—Compact, spreading, vigorous; very free flowering, never going out of bloom once it starts blooming under greenhouse conditions; flowers carried above foliage.

C. *Height from soil line.*—15 to 20 cm.

D. *Spread.*—40 to 45 cm at maturity. Leaf Size: 15 to 20 cm in length and 5 to 6 cm in width at the widest point; leaf size can vary greatly with cultural conditions. Quantity: Mature plant can have more than 20 leaves. Leaf Shape: Elliptical. Texture: Lower surface rugose with veins protruding and pubescent — upper surface rugose and pubescent. Margin: Finely crenate. Color: Young foliage top side 146B; under side 148D. Mature foliage top side 137A; under side 139D. Ribs and veins: Pinnate. Rib and vein color: 146A. Leaf tips: Obtuse. Leaf base: Acute.

Flowering description: Flowers open one at a time on the individual flower stalks.

A. *Fully expanded.*—35 to 40 mm.

B. *Stem.*—Single, reddish purple in color, long, slightly pubescent and round — several from a leaf midrib.

C. *Form.*—Funnel shaped, calyx deeply 5 parted with no tube, corolla cylindrical 5 lobed, lobes orbicular to ovate with 2 upper petals smaller and reflexed, and lower petals flattened. Results in flat appearing flower.

D. *Flower bud description.*—28 to 30 mm at maturity, tubular with the end larger in diameter than the rest of bud. 5 green calyx folded over basal end.

E. *Flowers borne.*—In clusters of 2 to 4 flowers per flower stalk with 3 the most common; carried above the foliage. Terminal flower opens first. Pedicels of the flowers in the inflorescence vary in length.

F. *Quantity of flowers.*—Mature plant can have more than 20 flower stalks open, with up to 4 flowers per stalk.

G. *Permanence.*—Long lasting, 10 days or longer.

Color:

A. *Tonality from a distance.*—Mid-blue with deep blue streaking out into the lower 3 petals. Eye is almost white.

B. *Upper surface of petals.*—91A with 90A streaking into lower petals.

C. *Under surface of petals.*—92B.

D. *Throat.*—155C with 90A streaking.

E. *Discoloration.*—Will fade to a lighter shade of blue.

Petals:

A. *Texture.*—Satin, glabrous.

B. *Appearance.*—Individually lobed with slight crenate margins, top 2 petals are reflexed and smaller than the 3 bottom petals which are slightly cupped.

C. *Arrangement.*—Regularly united into an almost circular shape.

D. *Persistence.*—10 days or longer. Remain on plant in dry form until picked.

E. *Fragrance.*—None.

Reproductive organs:

A. *Stamens.*—2 semi-fertile; 2 sterile. Anther shape: Flat, not interconnected like most fertile anthers. Anther color: Yellow. Filament: Purple cast; free standing from 5 mm on semi-fertile, white; free standing for 3 mm on sterile. Pollen color: White but very scant.

B. *Pistils.*—Stigma shape: 2 lobed flattened, rounded at ends of lobes. Stigma color: White. Stigma size: 2 mm across. Style color: White. Style size: 6 mm. Ovaries: Many, 12 mm, brownish purple.

Disease resistance: No disease problems to date.

Other important characteristics: Compact growth habit combined with the highly floriferous nature and ease of propagation makes Janus suitable for 10 cm pot plant production. The long lasting, non-shattering flowers of Janus and its pliable small leaves makes shipping easy. Lack of major insect and disease problems makes for a trouble free crop.

I claim:

1. A new and distinct cultivar of Streptocarpus plant named Janus, as described and illustrated, and particularly characterized by its compact growth habit, rosette form, violet blue flower color, floriferous habit, small pliable leaves, ease of propagation, and by its long lasting and non-shattering flowers.

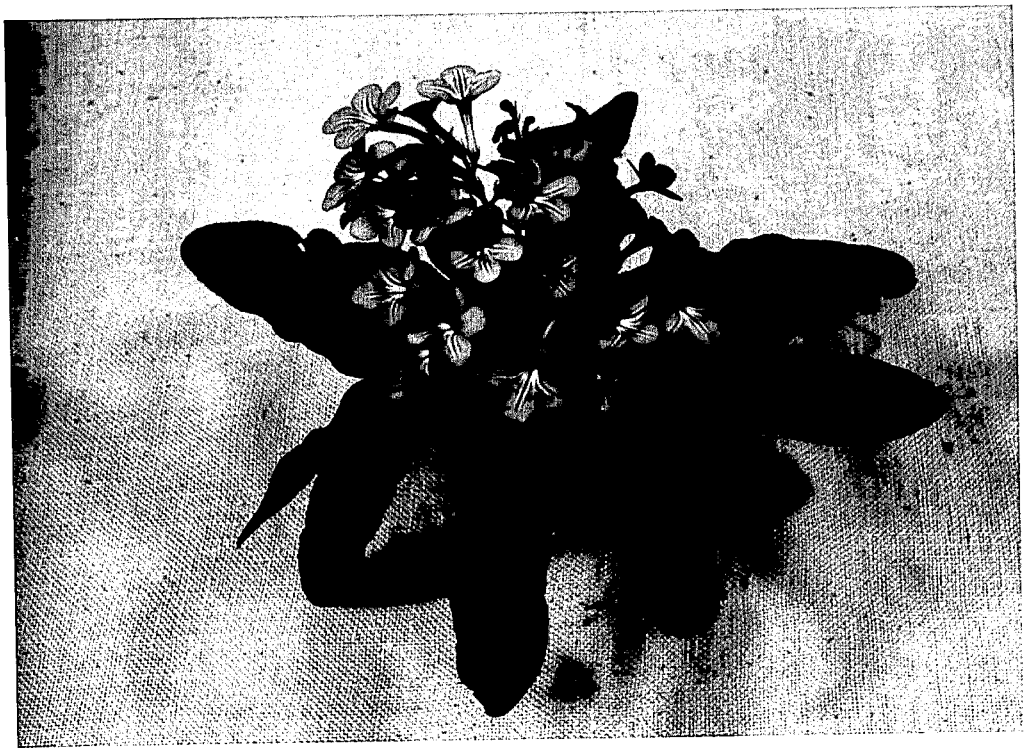

* * * * *